United States Patent
Cha et al.

(10) Patent No.: US 10,816,471 B2
(45) Date of Patent: Oct. 27, 2020

(54) FLUORESCENCE SIGNAL READING DEVICE HAVING SAMPLE FLOW DETECTING FUNCTION

(71) Applicant: BODITECH MED INC., Chuncheon-si, Gangwon-do (KR)

(72) Inventors: Min Seok Cha, Chuncheon-si (KR); Sang Hyun Park, Seoul (KR); Jae Min Lee, Chuncheon-si (KR); Byeong Chul Kim, Chunchon-si (KR); Joo Hyun Cho, Chuncheon-si (KR); Kie Bong Nahm, Seoul (KR)

(73) Assignee: BODITECH MED INC., Chuncheon-si, Gangwon-do (KR)

( * ) Notice: Subject to any disclaimer, the term of this patent is extended or adjusted under 35 U.S.C. 154(b) by 0 days.

(21) Appl. No.: 16/329,734

(22) PCT Filed: Mar. 24, 2017

(86) PCT No.: PCT/KR2017/003170
§ 371 (c)(1),
(2) Date: Feb. 28, 2019

(87) PCT Pub. No.: WO2018/043857
PCT Pub. Date: Mar. 8, 2018

(65) Prior Publication Data
US 2019/0195795 A1  Jun. 27, 2019

(30) Foreign Application Priority Data
Aug. 29, 2016  (KR) .................. 10-2016-0109912

(51) Int. Cl.
*G01N 21/64* (2006.01)
*G01N 33/543* (2006.01)
(Continued)

(52) U.S. Cl.
CPC .......... *G01N 21/645* (2013.01); *G01N 21/64* (2013.01); *G01N 33/487* (2013.01);
(Continued)

(58) Field of Classification Search
CPC ..... G01N 21/645; G01N 21/64; G01N 33/487
See application file for complete search history.

(56) References Cited

U.S. PATENT DOCUMENTS

| 2015/0004717 A1* | 1/2015 | McDevitt | ........... G01N 35/1002 436/501 |
| 2018/0275058 A1* | 9/2018 | Stern | ........................ G01J 3/44 |
| 2019/0003974 A1* | 1/2019 | Moynihan | ............ G01N 21/645 |

FOREIGN PATENT DOCUMENTS

| JP | 2009-300256 A | 12/2009 |
| JP | 2014-202755 A | 10/2014 |

(Continued)

OTHER PUBLICATIONS

International Search Report of corresponding Patent Application No. PCT/KR2017/003170—4 pages (Jun. 8, 2017).

*Primary Examiner* — Hugh Maupin
(74) *Attorney, Agent, or Firm* — Knobbe Martens Olson & Bear LLP

(57) ABSTRACT

A fluorescence reader includes a base frame having an open part formed at the front thereof so that a diagnostic cartridge is inserted therein and having an inner space therein, an optical module disposed in the inner space of the base frame, and disposed to be positioned above the diagnostic cartridge inserted through the open part to irradiate a light to the diagnostic cartridge; a driving module for moving the optical module; and a sensor module for sensing the insertion of the diagnostic cartridge and the position of the optical module. The fluorescence signal reader automatically calculates a measurement time when a user loads a solution, (Continued)

thus improving detection accuracy and shortening a detection time.

15 Claims, 20 Drawing Sheets

(51) Int. Cl.
*G01N 33/558* (2006.01)
*G01N 33/487* (2006.01)
(52) U.S. Cl.
CPC ..... *G01N 33/48707* (2013.01); *G01N 33/543* (2013.01); *G01N 33/558* (2013.01); *G01N 2021/6463* (2013.01)

(56) References Cited

FOREIGN PATENT DOCUMENTS

| KR | 10-2011-0002350 A | 1/2011 |
| KR | 10-2013-0012744 A | 2/2013 |
| KR | 10-2015-0031007 A | 3/2015 |

\* cited by examiner

FLUORESCENCE SIGNAL READING DEVICE HAVING SAMPLE FLOW DETECTING FUNCTION

TECHNICAL FIELD

The present disclosure relates to a fluorescence signal reading device, and more particularly, to a fluorescence signal reader, which can detect the flow of a sample solution analyzed by a lateral flow method to automatically calculate a flow time per actual unit length of a membrane, thus adjusting an optimum reaction time.

BACKGROUND ART

Various diagnostic kits are being developed to detect specific target substances in liquid samples such as blood samples for disease diagnosis. In particular, the diagnostic kit based on immunochromatographic assay is widely used to detect the status of disease or to monitor its development, and is being developed as a method for simply detecting a trace amount of biological materials in fields including but not limited to biological and environmental ones.

In such a diagnostic kit, a fluorescence substance is used as a labeling agent for detecting a target substance, and accordingly, a fluorescence reader for reading the fluorescence signal is widely used. Although such a fluorescence reader may perform accurate detection, its complicated structure may cause malfunctions and inaccurate results even by the trained user in many cases. Therefore, it is necessary to develop a device which is simple to use and also provides accurate results.

Korean Patent Publication No. 10-2015-0029290 relates to a diagnostic strip reader, and discloses a reader, which includes a stage on which a diagnostic strip including two or more detecting regions in the longitudinal direction thereof is placed; a light source and a light detector disposed at one side of the stage; and a moving means for moving the stage in the longitudinal direction thereof, and the diagnostic strip may be moved by the moving means, thus continuously obtaining signal values from two or more detection regions (reaction region and reference region).

In a lateral flow type detection scheme for qualitative measurements, one of factors for improving the accuracy is to scan a signal of a cartridge at a predetermined time. In the conventional method with a semi-automatic type measurement method, the operator loads a sample outside of the reader to wait for a predetermined duration before inserting it to the reader and push a scan operation button in order to obtain a result. For fast turnaround, the operator can employ a multitude of test pieces and prepare each one of them in rapid sequence. This method has the potential risk that the actual time of reaction as designated by the product developer may not be met appropriately. The actual time of reaction would depend on the individual operator's response to the timing device, on the time it takes the operator to insert the cartridge to press the button to initiate the testing cycle and on the actual time of the scan, all of which would compound to increase the inaccuracy of the final result. As such, a novel fluorescence reader without these shortcomings would prove useful.

DISCLOSURE

Technical Problem

The present disclosure is intended to solve the above problems, and an objective of the present disclosure is to provide a fluorescence signal reader including a configuration capable of implementing an improved method for automatically calculating a reaction time by detecting the sample flow through a membrane when a user loads a sample, instead of the existing semiautomatic methods where the operator pushes a button to initiate the measurement cycle.

Technical Solution

A fluorescence reader according to an embodiment of the present disclosure includes a base frame having an open part formed at the front thereof so that a diagnostic cartridge may be inserted therein and having an inner space therein; an optical module disposed in the inner space of the base frame, and disposed to be positioned above the diagnostic cartridge inserted through the open part to irradiate a light to the diagnostic cartridge; a driving module for moving the optical module; and a sensor module for sensing the insertion of the diagnostic cartridge and the position of the optical module.

Preferably, the optical module includes a module casing having a predetermined inner space therein; a light source disposed in the module casing and for generating excitation light; a light sensor part disposed in the module casing and for receiving emitted light generated from the diagnostic cartridge; and a light guide part disposed in the module casing and for guiding the excitation light and the emitted light; and the light guide part is configured to include one or more lens parts and mirrors to guide so that the excitation light generated from the light source is irradiated on the diagnostic cartridge, and to guide so that the emitted light generated from the diagnostic cartridge is incident to the light sensor part.

Preferably, the module casing is configured to have a rectangular box shape having an inner space therein, the light source is disposed on a lateral one surface of the inner surface of the module casing, the light sensor part is disposed on a rear one surface of the inner surface of the module casing, the light guide part is configured to include a first mirror, a second mirror, and a downward lens; and the first mirror refracts the excitation light irradiated laterally from the light source in the front direction thereof, the second mirror downwardly refracts the excitation light refracted in the front direction thereof, and the downward lens is configured so that the excitation light refracted downwardly passes therethrough to be irradiated on the diagnostic cartridge disposed under the lens, and the light processing part is configured to include an emitted filter, a lens, and a pin hole; and the emitted filter, the lens, and the pin hole are sequentially disposed between the first mirror and the light sensor part in the front-rear direction thereof to be disposed on a line that is lined with the first mirror, the second mirror, and the light sensor part.

Preferably, the module casing has a guide part on at least one side thereof, the guide part being protruding laterally, and the guide part includes an upper guide, a lower guide disposed under the upper guide being parallel with the upper guide, and a side guide disposed between the upper guide and the lower guide vertically formed on the outside.

Preferably, the driving module includes a motor for providing a rotational force; a driving shaft rotatably connected to the motor and disposed on at least one outside of the optical module to be extended in the front-rear direction thereof; and a carrier disposed between the optical module and the driving shaft to be coupled to the optical module and connected to the driving shaft, and the driving shaft has a spiral guide groove spirally extended and formed on the outer surface thereof, and the carrier is configured to have a guide protrusion part having one side coupled to one side of the optical module and having the other side inserted into the spiral guide groove, such that when the motor rotates to thereby rotate the driving shaft, the guide protrusion part is pushed by the spiral guide groove in the front-rear direction thereof to displace the carrier in the front-rear direction thereof, and accordingly, the optical module connected to the carrier is displaced in the front-rear direction thereof.

Preferably, the guide protrusion part has a plurality of protrusions protruded laterally and extended obliquely and includes a first guide protrusion part having the upper portion further protruded laterally to have the upper protrusion part, and a second guide protrusion part having the lower portion further protruded laterally to have the lower protrusion part, and the first guide protrusion part and the second guide protrusion part are alternately disposed so that the driving shaft is disposed between the upper protrusion part and the lower protrusion part.

Preferably, the carrier has an elastic part configured to have a plurality of bent parts between a first side coupled to the optical module and a second side having the guide protrusion part, such that the second side closely contacts the driving shaft and the guide protrusion part is stably inserted into the spiral guide groove.

Preferably, the driving module further includes a guide shaft extended in the front-rear direction thereof and disposed between the driving shaft and the optical module, the carrier has a guide hole penetrated in the front-rear direction thereof, and the guide shaft is configured to penetrate the guide hole so that the front-rear directional displacement of the carrier and the driving module are guided by the guide shaft.

Preferably, the sensor module includes a main board fixed to the base frame; and an interrupt sensor disposed on the main board, and the optical module further includes an interrupt protrusion part disposed to be protruded on one end outside of the module casing, the open part and the interrupt sensor, each is disposed in the opposite direction along the front-rear direction of the casing, respectively, and the optical module has an initial position in which the interrupt protrusion part is inserted into the interrupt sensor, and changes the position between the position of the open part and the position of the interrupt sensor.

Preferably, the sensor module further includes a sensing switch disposed under the main board, and the sensing switch generates an insertion signal of the diagnostic cartridge inserted by being configured to have the diagnostic cartridge press the sensing switch when the end portion of the diagnostic cartridge reaches a particular position after the diagnostic cartridge is inserted into the base frame through the open part.

Preferably, the base frame further includes a plate spring at least a part of which being protruded into an insertion space, and the plate spring put a pressure on at least a part of the diagnostic cartridge to fix the position of the diagnostic cartridge when the diagnostic cartridge is inserted into the insertion space.

Preferably, the diagnostic cartridge is provided with a tag for storing a predetermined information, and the fluorescence reader further includes a tag reader module capable of reading the tag provided in the diagnostic cartridge.

The fluorescence reader according to the present disclosure is configured in such a way to detect the time of the start of the reaction by reading the fluorescence signal from initial influx of fluorescence substances or reaction substances into the sensing zone via a membrane (e.g., Nitrocellulose membrane) after the user applies the sample, rather than by the user click of the start button or by the time the sample was loaded on to the cartridge.

In the aspect according to the above, the present disclosure includes the method for adjusting an analysis time of a sample in a lateral flow assay, and the lateral flow assay is performed using a cartridge having a strip mounted therein and a measurement window for exposing at least part of the strip where the sample develops, the method including: starting a lateral movement of the sample through the strip by loading the sample on the strip, the strip comprising a sample pad on which the sample is loaded, a membrane on which the sample is developed, and an absorption pad, measuring a first time when the sample starts the lateral flow to reach a first position of the measurement window; measuring the second time when the sample reaches a second position of the measurement window, and calculating the capillary flow rate by utilizing these results and the length of the measurement window, and comparing the corresponding value of the membrane as provided by a membrane manufacturer; and calculating the minimum reaction time by multiplying the capillary flow rate by the total length of the membrane.

After the duration as estimated in this disclosure, when the reaction is completed, the membrane of the measurement window is scanned with an optical module to calculate the concentration of the analysis substance utilizing the fluorescence intensity thus detected. With this embodiment, it is possible to expend the whole amount of the sample loaded on the sample pad of the strip, thus obtaining accurate and reproducible results.

Advantageous Effects

The fluorescence reader according to the present disclosure may detect the flow of the solution loaded in the developing medium to automatically calculate the flow rate of the membrane, thus improving reproducibility and accuracy of the detection and shortening the total analysis time.

Particularly, the fluorescence signal reader according to the present disclosure is configured to detect the fluorescence signal detected at the position (A in FIGS. 15A and 15B) which is the region of the exposed membrane (e.g., NC membrane) to which the sample solution reaches as a starting time and also to determine the time the sample to reach at the end position of the exposed membrane (C in FIGS. 15A and 15B), and to calculate accurately the total reaction time required, resulting in the reproducible and accurate analysis of the sample of interest, unlike the conventional method in which the time of loading the sample to the cartridge is used as the start time. In addition, it is possible to accurately detect the positions of the cartridge and the optical module, thus contributing to obtain the accurate and reproducible detection results.

DESCRIPTION OF THE INVENTION

Hereinafter, preferred embodiments according to the present disclosure are described with reference to the accompanying drawings.

Figure 1:
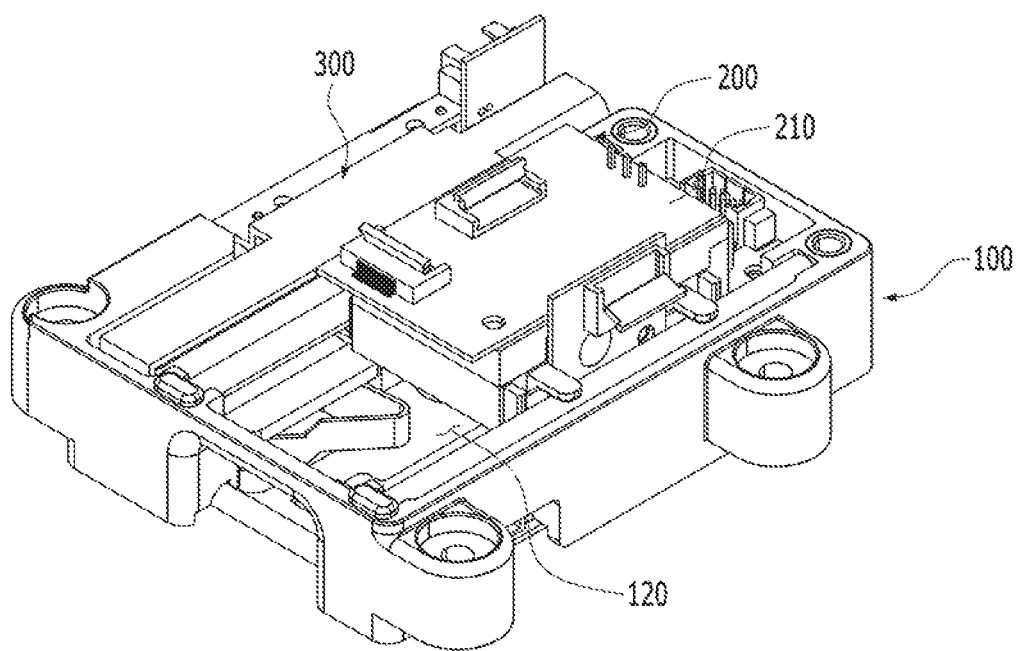
FIG. 1 is a diagram illustrating a fluorescence reader according to one embodiment of the present disclosure.
Figure 2:
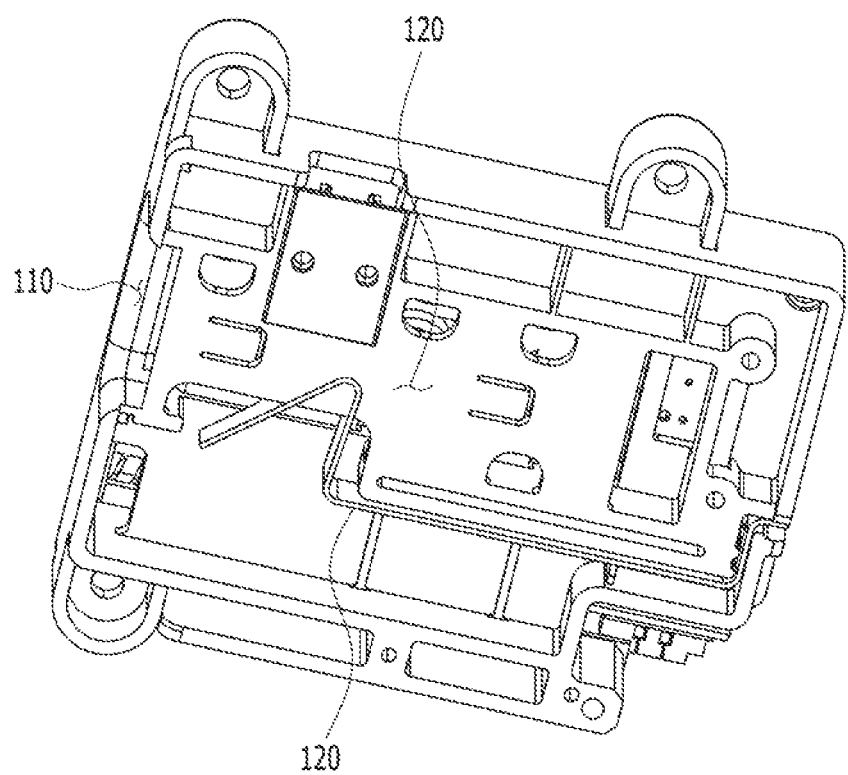
FIG. 2 is a diagram illustrating the fluorescence reader of FIG. 1 viewed from the bottom thereof.

FIGS. 1 and 2 are diagrams illustrating a fluorescence reader 1 according to the present disclosure. In FIG. 1, the X-axis direction refers to "front-rear direction," the Y-axis direction to "lateral direction," and the Z-axis direction to "height direction." Hereinafter, when there is a reference to "front-rear direction," "lateral direction," and "height direction," it is determined based on the direction indicated in FIG. 1.

The fluorescence reader 1 according to an embodiment of the present disclosure is configured to include a base frame 100, an optical module 200, a driving module 300, and a sensor module 400.

The base frame 100 constitutes at least one exterior of the fluorescence reader 1 according to the present disclosure. The base frame 100 is configured so that the optical module 200, the driving module 300, the sensor module 400, and various configurations are properly fixed or mounted thereto.

The base frame 100 has an open part 110 formed at one side thereof and has an insertion space 120 opened to the outside through the open part 110 so that a diagnostic cartridge may be inserted into the insertion space 120 through the open part 110.

The base frame 100 may also be provided with a fixing means to prevent the diagnostic cartridge from unnecessarily shaking or deviating from its desired position when the diagnostic cartridge is inserted into the insertion space 120. For example, as illustrated in FIG. 2, a plate spring 130 that is bent in a triangular shape and is protruded into the insertion space 120 may be provided to support the diagnostic cartridge so as to support the cartridge 120 inserted.

Meanwhile, the base frame 100 may be provided with a connector, etc. so that an electric device, a power supply, etc. may be connected thereto, but is not limited thereto.

Figure 3:
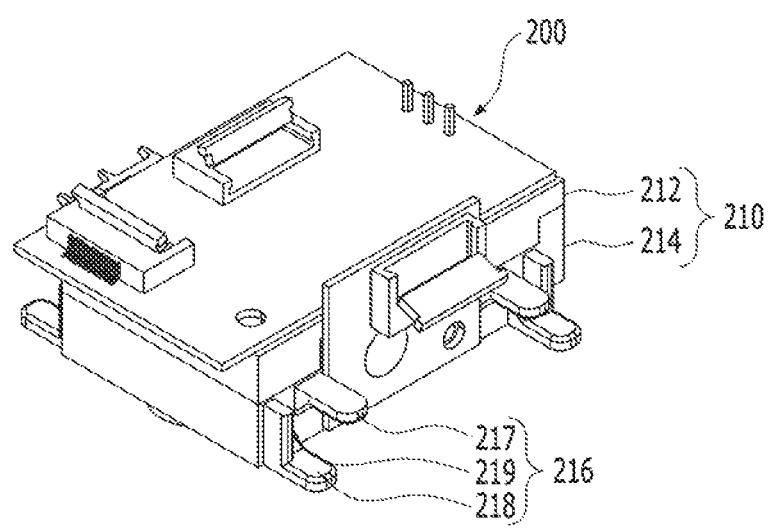
FIG. 3 is a diagram illustrating an optical module of the fluorescence reader according to one embodiment of the present disclosure.
Figure 4:
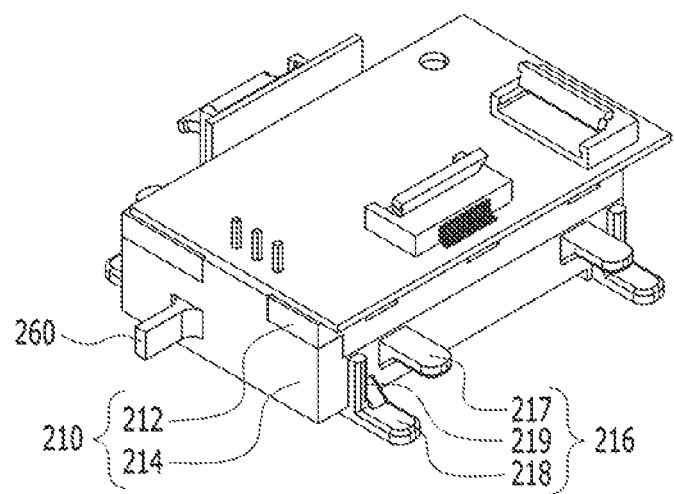
FIG. 4 is a diagram illustrating the optical module of FIG. 3 viewed from another direction thereof.
Figure 5:
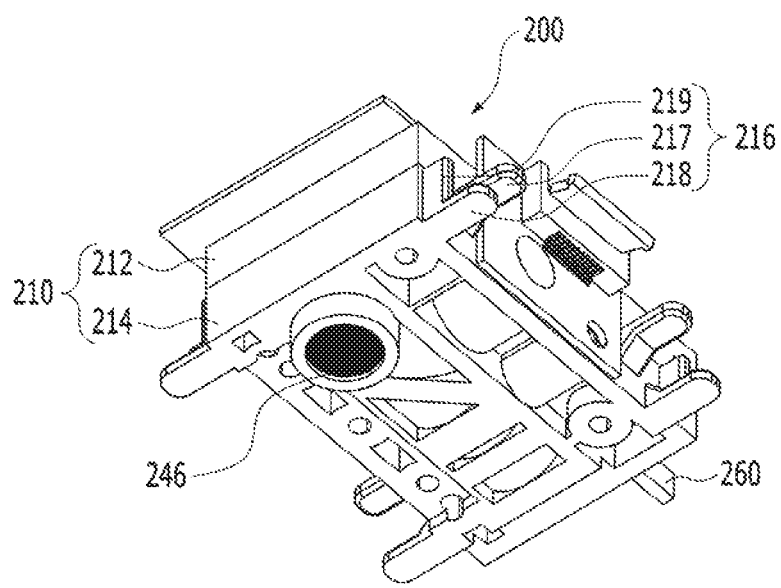
FIG. 5 is a diagram illustrating the optical module of FIG. 3 viewed from the bottom of another direction thereof.
Figure 6A:
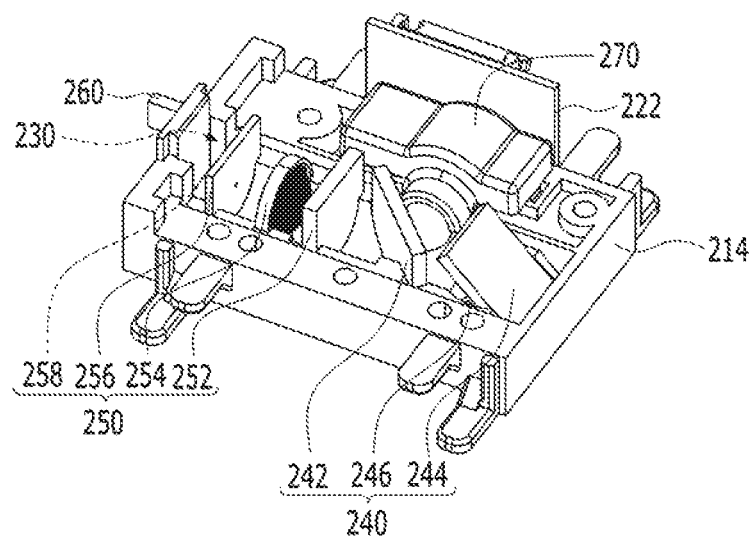
FIGS. 6A and 6b are diagrams illustrating an internal structure of the optical module of FIG. 3.

FIG. 3 is a diagram illustrating the optical module 200 of the fluorescence reader 1 according to one embodiment of the present disclosure, FIG. 4 is a diagram illustrating the optical module 200 of FIG. 3 viewed from another direction thereof, FIG. 5 is a diagram illustrating the optical module 200 of FIG. 3 viewed from the bottom of another direction thereof, and FIG. 6 is a diagram illustrating an internal structure of the optical module 200 of FIG. 3.

The optical module 200 is provided to irradiate a light to the diagnostic cartridge inserted into the base frame 100, and to irradiate the incident light to the sample labeled with fluorescence material, and to obtain the emitted light reflected thereby.

The optical module 200 is configured to include a module casing 210, a light source 220, a light sensor part 230, a light guide part 240, a light processing part 250, an interrupt protrusion part 260, and various PCBs and connectors.

The module casing 210 is configured as a casing in a box shape, and is configured to have a space formed therein so that the light source 220, the light sensor part 230, the light guide part 240, and the light processing part 250 can be included and installed therein. The module casing 210 has a rectangular three-dimensional shape, and may have a configuration in which an upper casing 212 and a lower casing 214 are coupled to each other, but is not necessarily limited thereto.

Meanwhile, a part of the bottom of the module casing 210 is configured to be penetrated so that a downward lens 246, which is described hereinafter, is disposed thereon. Therefore, the excitation light generated from the light source 220 in the module casing 210 is emitted downwards through the downward lens 246, and the emitted light generated from the bottom thereof can be incident into the module casing 210 through the downward lens 246.

Various boards and connectors may be prepared outside the module casing 210. The connector is prepared so that the light source 220, the light sensor part 230, etc. in the module casing 210 may exchange an electric signal with external electric devices, and may be connected to an electric terminal.

Meanwhile, the module casing 210 may have a guide part 216 disposed outside of the side portion thereof.

The guide part 216 is a member for stably guiding the displacement of the module casing 210 when the module casing 210 is displaced in the front-rear direction by a driving module 300, which is described hereinafter.

The guide part 216 is configured to include an upper guide 217, a lower guide 218, and a side guide 219. The upper guide 217 and the lower guide 218 have a certain distance separating the two in up-and down direction and are protruded laterally by a predetermined width in parallel. Preferably, the distance between the upper guide 217 and the lower guide 218 may correspond to a diameter of a first guide shaft 352, which is described hereinafter. The side guide 219 is disposed between the upper guide 217 and the lower guide 218 to be protruded outwardly by a predetermined width. The outer surface of the side guide 219 may form a vertical surface in up-and down direction For example, when a guide part having a complicated shape such as a circular shape or a curved surface is prepared, it is necessary to manufacture and assemble guide part very precisely. If such guide parts are not manufactured exactly as designed, or when a manufacturing error or an assembling error of a driving shaft occurs, a frictional force may become very large, and the frictional force exceeding a torque of a motor may cause a missed step on the gear and thereby, the optical module may not move to the desired position.

On the other hand, as in the present disclosure, the guide part 216 is configured to include the upper guide 217, the lower guide 218, and the side guide 219, thus firstly contacting a first guide shaft 352 which is described hereinafter, and thus reducing the friction. Therefore, the operation of the optical module 200 may be performed accurately and precisely.

In addition, the upper guide 217, the lower guide 218, and the side guide 219, which are configured to be simply protruded laterally further simplifies a manufacturing process. That is, the guide parts are formed of the structures that are simply protruded laterally without having a complicated shape such as a circular shape or a curved surface, thus not requiring high shape accuracy, and it is possible to manufacture them just with the molds of simple upper and lower plate structures without adding a separate slide core, thus providing further advantageous in manufacturing process.

The light source 220 is disposed inside of the module casing 210, and may generate excitation light having a predetermined wavelength by receiving a predetermined power. For example, the light source 220 may have a light emitting diode (LED) for generating light of a specific wavelength band, or may have a predetermined laser light source 220 for generating straight-line light, but is not necessarily limited thereto. The excitation light generated from the light source 220 is induced by the light guide part 240, which is described hereinafter, to be irradiated to the diagnostic cartridge. Therefore, the excitation light is incident to a fluorescence material contained in the sample loaded on the diagnostic cartridge, and the emitted light is generated by the fluorescence material. Meanwhile, a predetermined light source board 222 may be prepared to control the operation of the light source 220.

Unlike the conventional device, the device according to the present disclosure is configured in such a way that the cartridge does not move; the optical module moves. With conventional cartridge-moving systems, a structure corresponding to a conveying part for the cartridge is required to convey the cartridge, and a driving part and a conveying belt for moving it become lengthy, thus having a limitation for miniaturization. The present device is configured for conveying a small optical module, not conveying the cartridge, making it possible to simplify a configuration of the device enabling the miniaturization as a whole.

The light sensor part 230 is configured to collect the light radiating from the diagnostic cartridge. In an embodiment, the emitted light sensor part 230 uses a photodiode through which the emitted light is converted into an electrical signal. In another embodiment, the light sensor part 230 may consist of a photo detector, etc. as the light detector.

The light guide part 240 guides the excitation light generated from the light source 220 to irradiate the diagnostic cartridge, and at the same time, guides the emitted light generated from the diagnostic cartridge to be incident to the light sensor part 230. Accordingly, the light guide part 240 may be configured to include lenses and mirrors capable of controlling the light path.

The light processing part 250 may have various devices for amplifying the light signal, or modulating and converting the light. For example, the light processing part 250 may be configured to include an emission filter 252, a lens 254, and a pin hole 256, and may be configured to include various modulators, converters, etc.

Meanwhile, the light processing part 250 and the light guide part may not necessarily be separate members that are mutually exclusive. For example, when a predetermined lens, which is disposed on the light path to guide the light at the same time while adjusting the specification of the light, is prepared therein, the lens may be described as a light guide part and at the same time, the light processing part 250.

The interrupt protrusion part 260 may be prepared to be protruded to the front-direction on one end of the module casing 210. The interrupt protrusion part 260 has a protrusion part that is protruded to have a predetermined width and length. The interrupt protrusion part 260 controls the operation of an interrupt sensor 420, which is be described hereinafter, and specific configurations and operations thereof are described hereinafter.

Figure 6B:
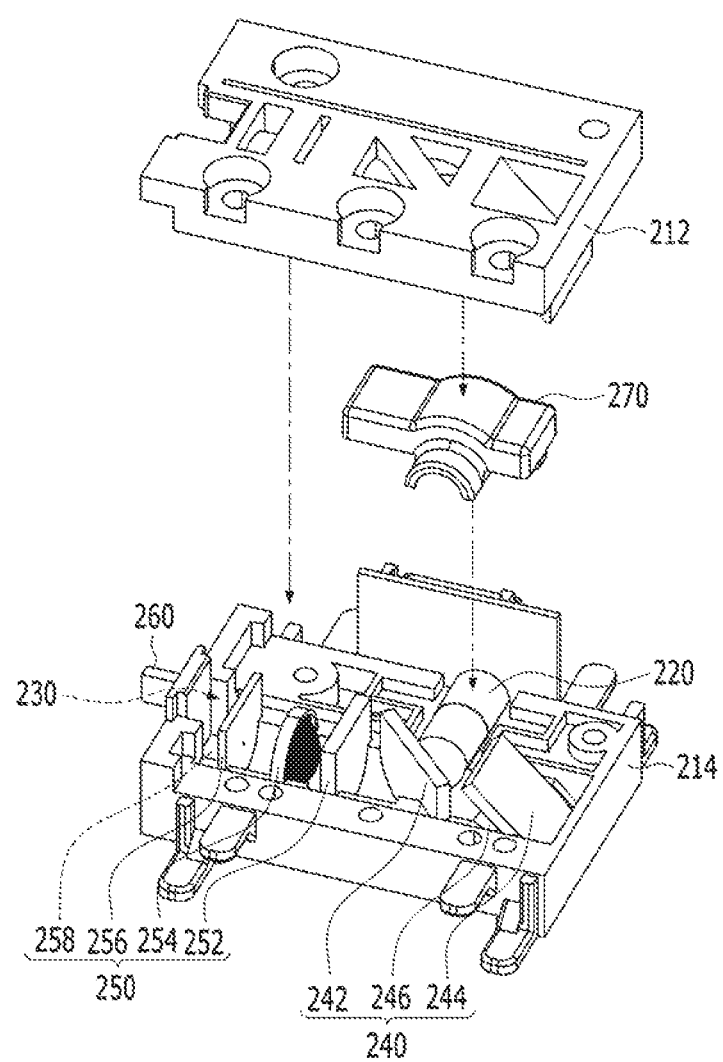

The laser heat-dissipating part 270 is configured to cover at least a part of the light source 220, or to be connected to at least a part thereof. Preferably, the laser heat-dissipating part 270 is disposed on the upper portion of the light source 220 to have the lower surface corresponding to a shape of the upper portion of the light source 220 to cover, press, and surround at least a part of the upper portion of the light source 220. In addition, when the upper portion of the laser heat-dissipating part 270 may be pressed by the upper casing 212 to cover the upper casing 212 and fix to the lower casing 214, the laser heat-dissipating part 270 may be pressed by the upper casing 212 to cover and closely contact the light source 220. Such a coupling structure is illustrated in FIG. 6B.

In the light source 220, as an operating time becomes longer, an internal temperature increases, and the laser characteristic drifts as the temperature increases such that there is a possibility that the output of the laser decreases. Therefore, in order to generate a stable laser output, a scheme is required that would conduct the heat from the laser head away by bringing in a structure made of materials with high thermal conductivity, such as aluminum, into contact with the laser head. However, it is difficult to precisely process a material such as aluminum by mold injection, and therefore, it may be difficult to dispose optical devices such as a first mirror 242, a second mirror 244, the downward lens 246, the lens 254, and the pin hole 256 in the optical module at the accurate positions.

Therefore, the upper casing 212 and the lower casing 214 are made of acetal (POM) material or PC material suitable for precise injection molding, and the laser heat-dissipating part 270 for performing laser heat-dissipating is made of an aluminum material by separating a part of the upper casing 212, thus achieving a precise structure at the same time together with heat-dissipating effect.

In addition, if the lower casing 214 and the upper casing 212 were fabricated with heat-dissipating materials, the heat-dissipating effect could improve, but the precision of locating the light source 220 within the heat-dissipating structure is reduced, such that the contact surfaces thereof may not be in contact with each other due to tolerance, while according to an embodiment, the laser heat-dissipating part 270 is prepared on the light source 220, such that even when there occurs a difference in the size of the light source 220, the heat-dissipating against the surface temperature of the light source 220 may be possible up to a tolerance of about 0.2 mm due to the pressed structure of the upper casing 212.

An internal structure of the optical module 200 according to an embodiment may be specifically configured as illustrated in FIG. 3. FIG. 3 is a diagram illustrating an internal structure of the optical module 200 by eliminating the upper casing 212 of the module casing 210.

Specifically, the module casing 210 is formed in a rectangular box shape having a space therein, and the light source 220 and the light sensor part 230 may be disposed at one side inside the module casing 210, respectively. First, the light source 220 may be disposed on lateral one side surface inside the module casing 210, and the light sensor part 230 may be disposed on the rear one end portion surface inside the module casing 210.

The light guide part may be configured to include the first mirror 242, the second mirror 244, and the downstream lens 246.

First, the first mirror 242 is laterally inclined with respect to the path of the excitation light so that the excitation light incident from the lateral direction by the light source 220 changes the direction forwardly. Specifically, when the excitation light radiating from the light source 220 is incident in the Y-axis direction on an XY plane, the first mirror 242 may have an orientation angle that is perpendicular to the XY plane and is inclined by 45° with respect to the Y-axis. The first mirror is made of a dichroic mirror and has a filter function and a reflector function at the same time. That is, the first mirror is an element for reflecting the excitation light of 635 nm laser light according to an embodiment of the present disclosure and allowing the emitted light of 650 nm through according to an embodiment of the present disclosure.

Next, the second mirror 244 is a total reflection mirror, and is inclined downwardly with respect to the path of the excitation light so that the excitation light irradiated forwardly changes the path downwardly. Specifically, when the excitation light refracted by the first mirror 242 is incident in the X-axis direction on the XY plane, the first mirror 242 may have an orientation angle that is perpendicular to the XZ plane and is inclined by 45° with respect to the X-axis.

The downward lens 246 is prepared under the second mirror 244 so that the excitation light passes through the downward lens 246 to irradiate the diagnostic cartridge disposed under the lens 246.

The light processing part 250 is configured to include the emission filter (bandpass filter) 252, the lens, and the pin hole 256. The emission filter 252, the lens, and the pin hole 256 may be disposed between the first mirror 242 and the light sensor part 230. At this time, the emission filter 252, the lens, and the pin hole 256 may have the arrangement in which the emission filter 252, the lens, and the pin hole 256 are sequentially arranged on the same line as the arrangement of the first mirror 242 and the second mirror 244, respectively. Therefore, after the incident emitted light is appropriately processed, it may be incident into the light sensor part 230. The emission filter 252 removes a range wavelength that is not specific emitted light, and the pinhole 256 may have a predetermined hole size so that only the emitted light within a specific path is incident into the light sensor part 230. A converter is provided in the light sensor part, and the light incident to the light sensor part is converted into a voltage signal through the converter.

Figure 7:
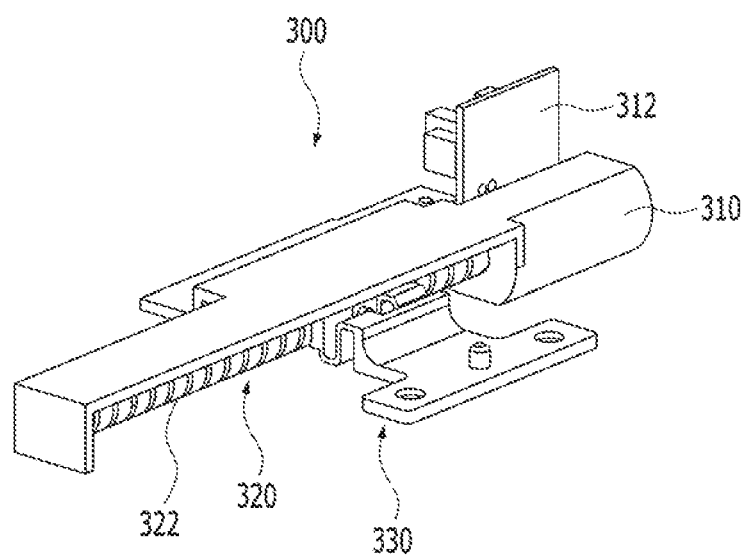
FIG. 7 is a diagram illustrating a structure of a driving module of the fluorescence reader according to one embodiment of the present disclosure.
Figure 8:
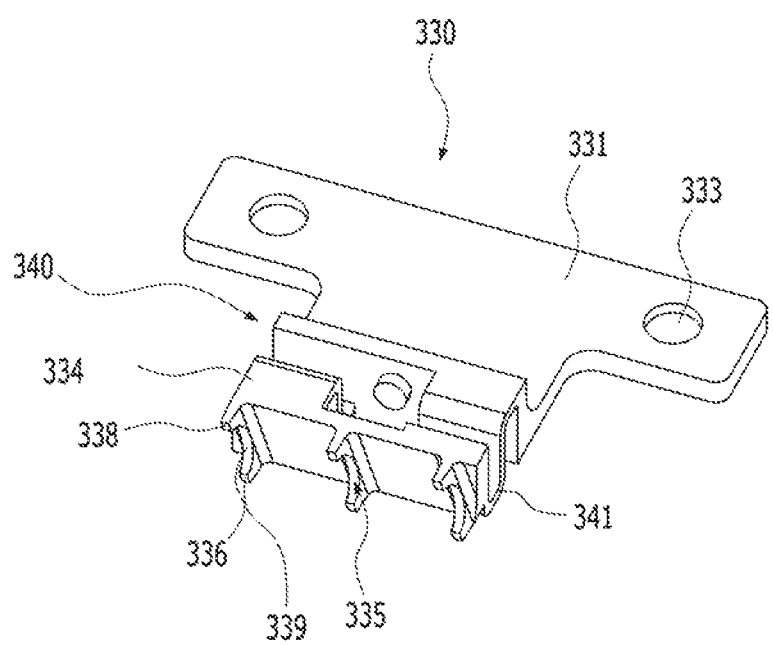
FIG. 8 is an enlarged diagram of a carrier of the driving module.
Figure 9:
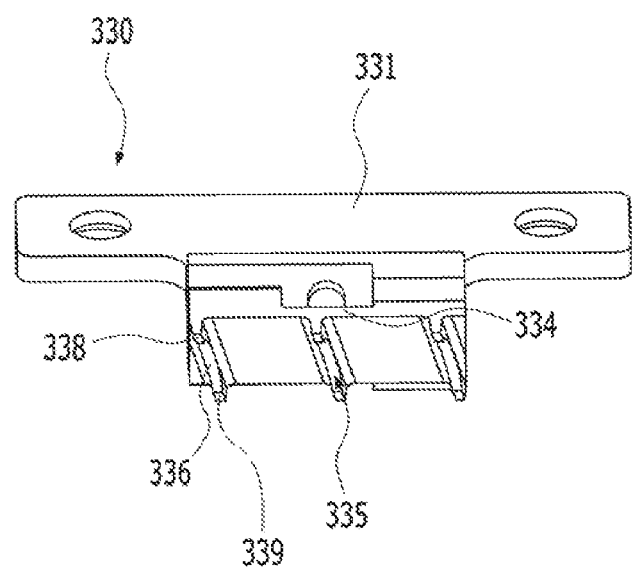
FIG. 9 is a diagram illustrating the carrier of FIG. 8 viewed from the side direction thereof.
Figure 10:
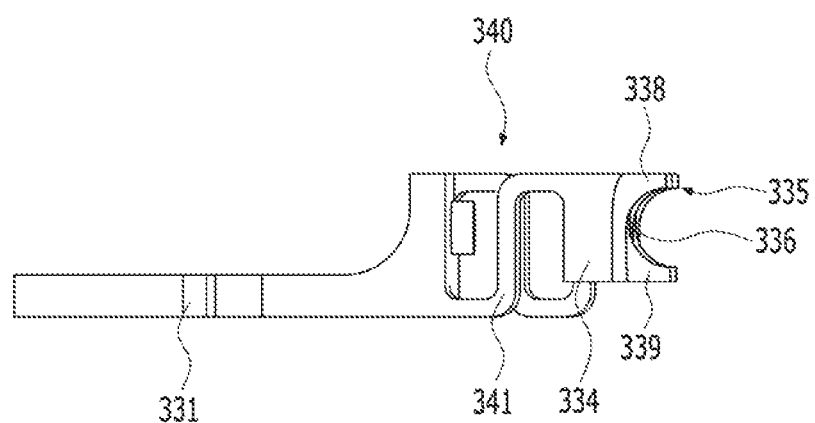
FIG. 10 is a diagram illustrating the carrier of FIG. 8 viewed from the front direction thereof.
Figure 11:
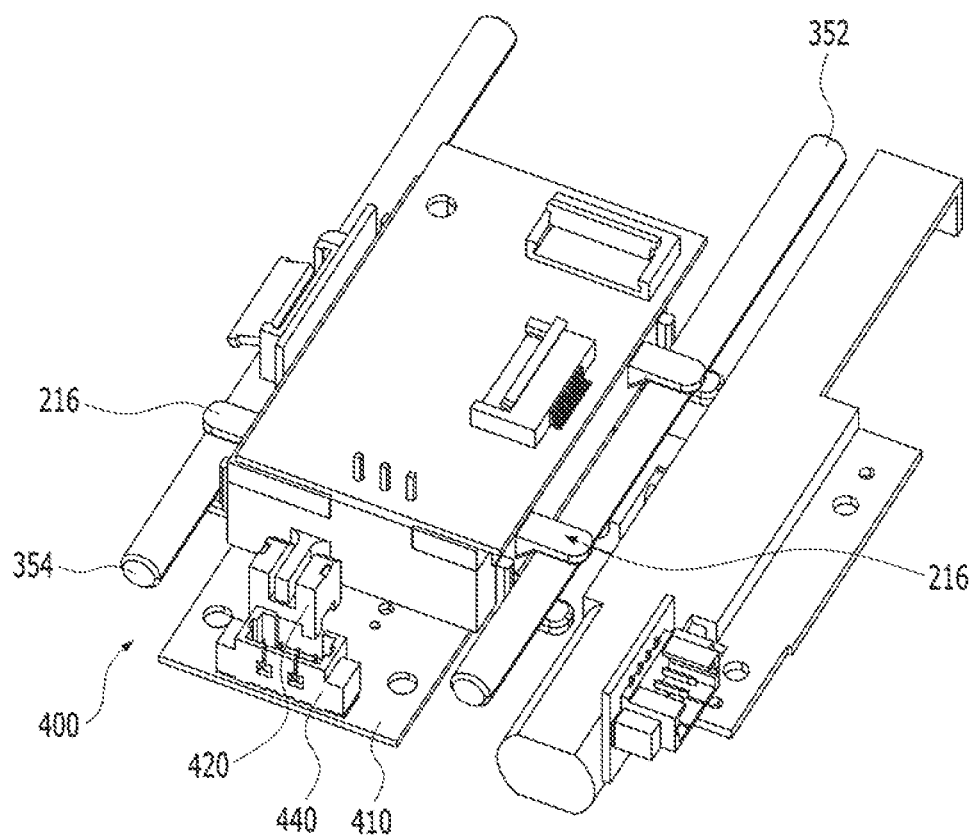
FIG. 11 is a diagram illustrating a connection structure between the driving module and the optical module.
Figure 12:
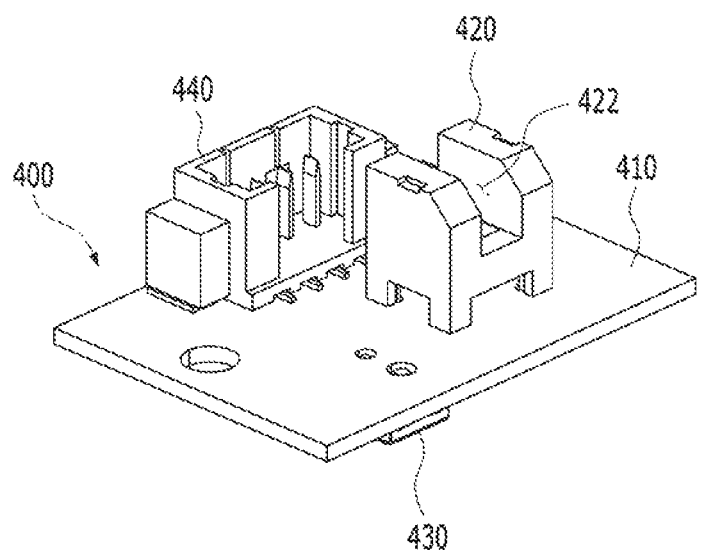
FIG. 12 is a diagram illustrating a sensor module.
Figure 13:
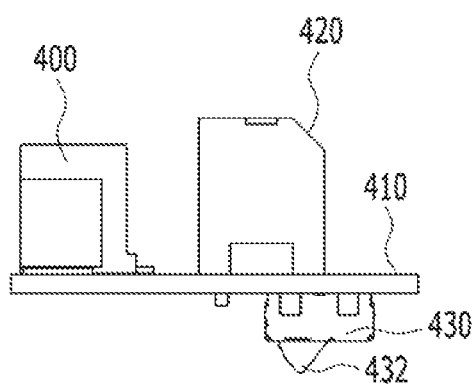
FIG. 13 is a diagram illustrating the sensor module of FIG. 12 viewed from the side direction thereof.

FIG. 7 is a diagram illustrating a structure of the driving module 300 of the fluorescence reader 1 according to the present disclosure, FIG. 8 is an enlarged diagram of a carrier 330 of the driving module 300, FIG. 9 is a diagram illustrating the carrier 330 of FIG. 8 viewed from the side direction thereof, FIG. 10 is a diagram illustrating the carrier 330 of FIG. 8 viewed from the front direction thereof, and FIG. 11 is a diagram illustrating a connection structure between the driving module 300 and the optical module 200.

The driving module 300 has a device for supplying power or transmitting power for displacing the optical module 200, or a device for guiding the displacement of the optical module 200. Specifically, the driving module 300 may be configured to include a motor 310, a driving shaft 320, the carrier 330, and a guide shaft.

The motor 310 is prepared to receive a predetermined power to generate a torque. The motor 310 may be disposed on one side edge portion in the inner space of the casing.

The driving shaft 320 has a predetermined shaft connected to the motor 310 to rotate. The driving shaft 320 is disposed on at least one outside of the optical module 200 to be extended in the front-rear direction in parallel with the optical module 200.

The driving shaft 320 has a spiral guide groove 322 formed on the outer surface thereof to be extended spirally. The spiral guide groove 322 has a spiral groove extended longitudinally around the outer surface of the driving shaft 320 in the circumferential direction thereof. It is preferable that the depth, width, and spiral period (longitudinal interval) of the spiral guide groove 322 are uniform.

The carrier 330 is a member coupled to one side of the optical module 200, and is a member for connecting the optical module 200 and the driving shaft 320 to achieve the front-rear directional displacement of the driving module 300 using the rotational force transmitted to the driving shaft 320.

The carrier 330 has one side coupled to the optical module 200, and has the other side engaged with the spiral guide groove 322. A predetermined elastic part 340 may be prepared between one side and the other side of the carrier 330. Hereinafter, a side coupled to the optical module 200 is referred to as a first side 331, and a side engaged with the spiral guide groove 322 is referred to as a second side 334.

The first side 331 of the carrier 330 may be configured to include a predetermined protrusion 332 or a groove 333 to be fixed to the module casing 210. Therefore, when the carrier 330 and the optical module 200 are coupled to each other to be integrally configured, and when an external force is applied to the carrier 330, the carrier 330 and the optical module 200 may be displaced together at the same time.

The second side 334 of the carrier 330 is configured to have a guide protrusion part 335 that may be inserted into the spiral guide groove 322.

Specifically, the guide protrusion part 335 may be configured to have a shape having a plurality of protrusions that are protruded laterally and diagonally extended by corresponding to a shape of the spiral guide groove 322. The front-rear directional interval between the plurality of guide protrusion parts 335 is configured to correspond to the front-rear directional interval of the spiral guide groove 322 when viewing the driving shaft 320 laterally. Therefore, the plurality of guide protrusion parts 335 are inserted into the spiral guide groove 322 at a position facing the second side 334 of the carrier 330, respectively.

Preferably, the guide protrusion part 335 is configured so that a curved surface having a "C" shape 336 is formed on the side surface thereof. That is, the guide protrusion part 335 is configured to have an upper protrusion part 338 further protruded on the upper portion of the side surface laterally, and a lower protrusion part 339 further protruded under the side surface laterally; and to dispose the curved surface having the "C" shape 336 between the upper protrusion part 338 and the lower protrusion part 339. Therefore, when viewing the guide protrusion part 335 in the front-rear direction thereof, it may be confirmed that the curved surface having the "C" shape 336 is formed as illustrated in FIG. 10. The driving shaft 320 is inserted into the curved surface having the "C" shape 336. Therefore, the closely contact area and the engagement area between the guide protrusion part 335 and the driving shaft 320 may become larger, thus further improving the power transmission effect.

The elastic part 340 is a part between the first side 331 and the second side 334 of the carrier 330, and is prepared to apply elasticity between the first side 331 and the second side 334. Preferably, a configuration of the elastic part 340 may have a structure having a plurality of bent parts 341. The carrier 330 has the elastic part 340, and is made of a material having elasticity such as plastic or synthetic resin, thus having a restoring force against a lateral pressure. As a result, the guide protrusion part 335 and the driving shaft 320 may closely contact with each other more effectively, thus further improving the power transmission effect.

Preferably, the shape of the bent part 341 constituting the elastic part 340 may be configured to have a "⊒" shape rotated by 90° so as to apply an elastic force laterally. Explaining it in other shapes, it may be understood to be configured to have a shape in which one or more "n"-shaped and "u"-shaped bent parts 341 are combined.

Preferably, as illustrated in FIG. 8, the front thereof may have a shape in which the "n"-shaped bent part 341 followed by the "u"-shaped bent part 341 are formed in the direction of from the first side 331 to the second side 334 (a shape in which the horizontally symmetric "⊒" shape is rotated by 90°), and conversely, the rear thereof may also have a shape in which the "u"-shaped bent part 341 followed by the "n"-shaped bent part 341 are formed in the direction of from the first side 331 to the second side 334 (a "⊒" shape rotated by 90°). Therefore, a more uniform elastic force may be laterally applied thereto.

The guide shaft 350 may have a predetermined beam disposed on both outsides of the optical module 200, respectively to be extended in the front-rear direction. For example, a first guide shaft 352 disposed between the driving shaft 320 and the optical module 200, and a second guide shaft 354 disposed on the opposite side thereof may be prepared therein. Meanwhile, the first guide shaft 352 may be placed on the upper portion of the carrier 330, as illustrated in FIG. 11, or may also be placed under the first guide shaft 352, or may also penetrate the carrier 330.

As described above, the guide part 216 protruded laterally is prepared on both side portions of the module casing 210, and the guide part 216 is configured to include the upper guide 217, the lower guide 218, and the side guide 219. The first guide shaft 352 is configured to contact the upper guide 217 and the lower guide 218 vertically, and to have one side portion contact with the side guide 219. At this time, since the first guide shaft 352 has a circular cross section, the first guide shaft 352 may be in line contact with the upper guide 217, the lower guide 218, and the side guide 219 in three directions, thus reducing a frictional area. Therefore, even when a torque of the motor is small, the optical module 200 may be simply conveyed, and the out-of-phase phenomenon due to friction may be prevented. In addition, advantages in manufacture are as described above.

The sensor module 400 is configured to include a sensor for sensing the insertion of the diagnostic cartridge and the position of the optical module 200. The sensor module 400 is configured to include a main board 410, an interrupt sensor 420, and a sensing switch 430.

The main board 410 may have a predetermined PCB that is disposed to be coupled in the base frame 100.

Preferably, the main board 410 may be disposed at an opposite position to the open part 110 of the base frame 100. The interrupt sensor 420 may be disposed on the upper portion of the main board 410, and the sensing switch 430 may be disposed under the main board 410. In addition, a predetermined connector 440 may also be prepared thereon.

The interrupt sensor 420 has a sensor having a predetermined insertion groove 422 formed at the front thereof. That is, the interrupt sensor 420 has the insertion groove 422 formed at the front thereof to recess a part of the front thereof, and when a predetermined device or an obstacle is inserted into the insertion groove 422, it may have a predetermined sensor for generating a signal or blocking the signal.

The interrupt protrusion part 260 provided in the optical module 200 may be inserted into the insertion groove 422 formed in the interrupt sensor 420. A distance between the interrupt sensor 420 and the interrupt protrusion part 260 varies as the optical module 200 displaces, and when the optical module 200 is adjacent to the main board 410, the interrupt protrusion part 260 is inserted in the interrupt sensor 420. The interrupt sensor 420 may generate a predetermined signal or stop the signal when the interrupt protrusion part 260 has been inserted into the interrupt sensor 420. Specifically, the interrupt sensor 420 according to the present disclosure may prevent the out-of-phase of the optical module 200. The out-of-phase is that the optical module 200 does not move as accurately as the instructed step along a rail. In order to solve it, a reference position is determined to move from the position by the instructed step, and the interrupt sensor 420 is for recognizing the reference position. That is, when the interrupt protrusion part 260 provided in the optical module 200 is inserted into the insertion groove 422 formed in the interrupt sensor 420, the reference position is recognized, and before the optical module is moved from one point to another point, it firstly moves to the reference position, and moves from here by the instructed step.

The sensing switch 430 has a predetermined switch for sensing whether the diagnostic cartridge has been inserted up to an accurate depth in the base frame 100.

For example, the sensing switch 430 may be pressed by the diagnostic cartridge to generate a signal when the diagnostic cartridge has been inserted up to a predetermined depth to reach the position capable of appropriately performing the sensing.

Accordingly, when the diagnostic cartridge is inserted up to the appropriate depth in an insertion space 120 through the open part 110 to reach an accurate position, the sensing switch 430 may be disposed on the end position of the insertion space 120 so that the diagnostic cartridge may push and press the sensing switch 430. Herein, that is, the end position means a position opposite to the open part 110. At this time, the sensing switch 430 may be configured to include a triangular button 432 in a triangular shape having a predetermined inclined angle so as to have a configuration that is pushed and pressed by the edge of the diagnostic cartridge.

As described above, the interrupt sensor 420 may be provided on the upper portion of the main board 410 and the sensing switch 430 may be provided under the main board 410 to be integrally configured, thus preventing a reduction in position accuracy due to an assembly error. That is, for example, when the interrupt sensor 420 and the sensing switch 430 independently move or are independently assembled, respectively, the possibility of occurring an error may be increased, but according to the present disclosure, the interrupt sensor 420 for sensing the position of the optical module 200 and the sensing switch 430 for sensing the position of the diagnostic cartridge may be provided on one main board 410 together, thus reducing the possibility of occurring an error and performing accurate detection.

Hereinafter, an operation of the fluorescence reader 1 according to the present disclosure is described.

Figure 14:
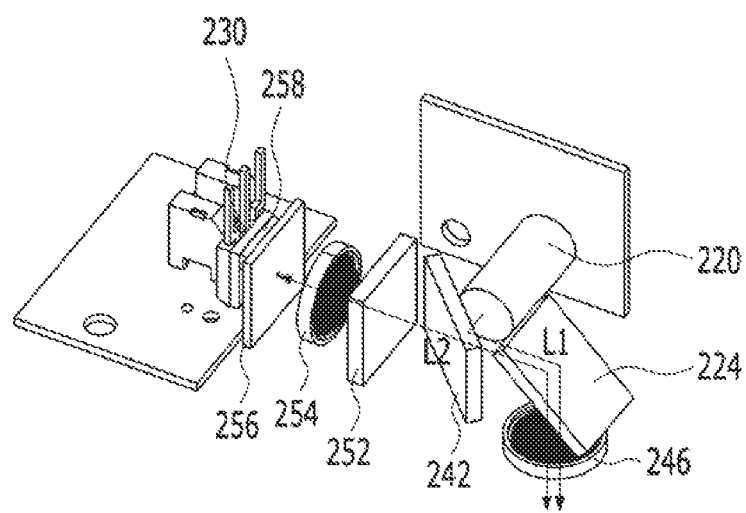
FIG. 14 is a diagram illustrating the paths of excitation light and emitted light in the optical module.

First, referring to FIG. 14, the paths of the excitation light and the emitted light in the optical module 200 is described.

The excitation light generated from the light source 220 disposed on the side portion in the module casing 210 has a same path as indicated by the arrow L1. First, the excitation light irradiated laterally has a lateral light path. The excitation light is incident to the first mirror 242 to changes the path in the front direction thereof, that is, in the direction in which the open part 110 is disposed. Then, when it is incident to the second mirror 244, the path is changed downwardly. The excitation light irradiated downwardly passes through the downward lens 246 to be irradiated to the sample in the diagnostic cartridge disposed under the lens 246.

The sample in the diagnostic cartridge contains a predetermined fluorescence substance, such that when the excitation light is incident to the sample, the emitted light is generated. The emitted light is emitted upwardly, and passes through the downward lens 246 to be incident to the second mirror 244.

Meanwhile, the emitted light has the same path as indicated by the arrow L2. The emitted light passes through the emission filter 252, the lens, and the pin hole 256 to be incident to the light sensor part 230. Accordingly, the light sensor part 230 may detect the emitted light. The light incident to the light sensor part is converted into a voltage signal via the converter provided herein.

Hereinafter, displacement of the optical module 200 by the driving module 300 is described.

As described above, the carrier 330 is fixed to the module casing 210 of the optical module 200, and the carrier 330 and the driving shaft 320 are connected to each other by the guide protrusion part 335 of the carrier 330 and the spiral guide groove 322 of the driving shaft 320. When the driving shaft 320 rotates by the rotational force of the motor 310, the spiral guide groove 322 rotates together, and it may be confirmed that when viewed from the side surface contacting the carrier 330, an oblique-shaped groove is displaced in the front-rear direction thereof. Therefore, the carrier 330 may be displaced in the front-rear direction thereof, and the optical module 200 connected to the carrier 330 may be displaced in the front-rear direction thereof.

According to such a configuration, a displacement distance of the carrier 330 and the optical module 200 may be controlled according to the RPM of the motor 310, thus performing an accurate control of the displacement distance of the optical module 200. In addition, as described above, the carrier 330 may be strongly in close contact with the driving shaft 320, thus effectively transmitting power and achieving an accurate control of the displacement distance more effectively. In addition, the guide shaft 350 may be further prepared to stably guide the displacement of the optical module 200, thus preventing the deviation, the out-of-phase, etc. of the optical module 200.

The fluorescence reader according to the present disclosure may be configured to detect the fluorescence signal, which is detected when mixed solution has moved to the exposed membrane (e.g., NC membrane), as the start time and to determine whether to pass through the exposed membrane, rather than the time of loading the solution mixing the sample with buffer solution by a user on the sample pad of the cartridge so as to calculate an accurate reaction time, thus obtaining accurate and reproducible detection results.

Figure 15A:
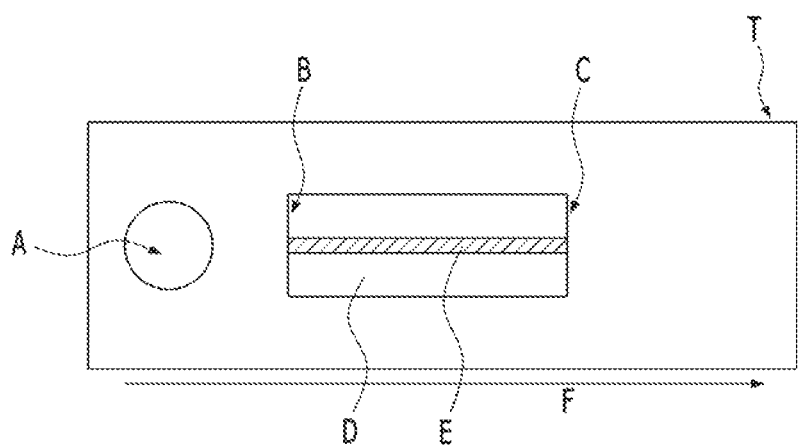
FIG. 15A is a diagram graphically illustrating a cartridge 10, which includes a sample inlet A, first and second positions B, C of a measurement window, and a membrane D, used in the fluorescence reader according to the present disclosure, and F indicates a lateral flow direction and E indicates a scanning part.
Figure 15B:
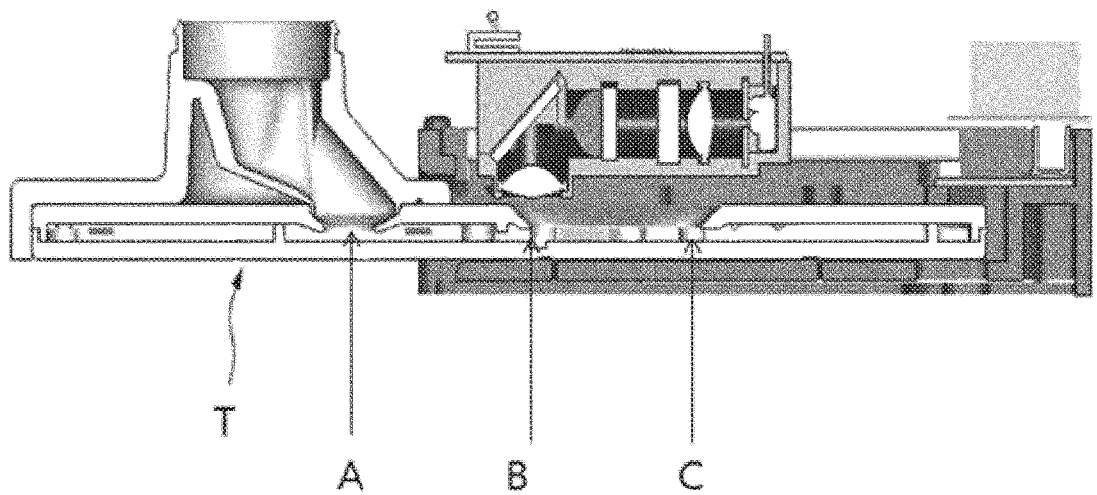
FIG. 15B is a cross-sectional diagram of the fluorescence reader according to an embodiment of the present disclosure in which the cartridge as in FIG. 15A is mounted therein.

Hereinafter, an operation of the fluorescence reader 1 according to one embodiment of the present disclosure when the diagnostic cartridge is inserted therein and the sample detected is described in detail with reference to FIGS. 15A and 15B. The cartridge 10 having an adapter for loading a sample is inserted into the fluorescence reader 1 according to the present disclosure. The cartridge is mounted with a strip, and the strip generally includes a sample pad on which the sample is loaded, a membrane for developing the sample (e.g., nitrocellulose membrane) through which the sample is moving/developed, and an absorption pad on which an extra sample solution having moved through the membrane is absorbed. When a sample is loaded onto the sample pad through the sample inlet A of the cartridge inserted into the fluorescence reader for analysis, the sample starts to move F in a lateral flow method, and reaches the membrane. Then, an optical system moves to a first position B of the strip to collect the fluorescence signal to confirm the start time (a first time), and then moves to a second position C to collect the fluorescence signal at this point to confirm the end time (a second time). In this case, the cartridge sensing switch 430 and the interrupt sensor 420 are utilized for convey to the accurate position. It is designed such that the reader starts to measure when the cartridge is inserted into the insertion space 120 without an error, and the optical module 200 is moved to the start point/position and the end point/positon after the interrupt protrusion part 260 is accurately inserted into the interrupt sensor 420, thus calculating an accurate lateral flow time.

For example, the flow time of a solution through the membrane provided by a manufacturer (Hi-Flow Plus Membrane, HF180, Merck Millipore) takes about 180 seconds to move 4 cm of the nitrocellulose membrane. The flow or wicking that occurs upon development in the lateral flow is a phenomenon in which the liquid moves by a capillary force along the surface of a fiber that constitutes a porous membrane. This flow varies depending on the characteristics of the liquid such as the surface tension, viscosity, and density of the liquid, that is, a sample, the interaction between the liquid and the membrane, the geometric shape of a pore structure of the membrane, etc. Therefore, a given time has a difference of about several seconds due to the reason as described above when the flow is initiated by an actual solution, thus the distance of a liquid sample moves through the membrane during the same period of time are not identical and thus a total amount of the sample flowing through the cartridge is also changed.

That is, if the reaction time is calculated according to the flow time provided by the manufacturer, for a membrane having a total length of 4 cm and given unit time of 45 seconds, a minimum reaction time (analysis time) required for sample starting from a sample pad to move through the membrane to the end of the membrane is 3 minutes.

However, in actual experimental conditions, the flow rate may vary due to the factors as described above. For example, assuming that the flow rate, which is a time required for flow through the membrane of 1 cm, is reduced to 50 seconds (flow rate), the value of 1.1 is obtained by comparing the flow rate with the given unit time, and then the actual time required is calculated as 50 seconds/cm×4 cm=200 seconds, that is, the minimum reaction time required is adjusted to 3 minutes 20 seconds.

In addition, the reaction time described above is a minimum reaction time and a reference time may be set for optimum results. In general, the reference time is a reaction time enough for allowing the entire liquid sample loaded onto the strip to flow through the membrane and is important for obtaining accurate and reproducible test results. In an embodiment according to the present disclosure, a value between the 2 and 4 times the length of the membrane is used. For example, when the optimum reaction time calculated according to the given flow rate, that is, the reference time, is 10 minutes, this is a time needed for moving about 3.3 times the length of the membrane (13.33 cm in total). In this case, the adjusted reference time of 11 minutes and 6.6 seconds (50 seconds/1 cm×13.33 cm) is required for the same amount of sample to flow through the membrane for the reference time of 10 min.

Therefore, so as to apply the accurate reaction time according to the type of the sample, etc., as described in the present disclosure, accurate results may be obtained when using the total reaction time, that is, the adjusted reference time by utilizing the measured time. That is, it is possible to reduce the total reaction time when the lateral flow is developed faster than a predetermined time, and to increase the total reaction time when it is slower than the predetermined time, thus the lateral flow assay can be performed for a sufficient time so that all the samples loaded move through the membrane.

Applying a uniform reaction time may result in an insufficient reaction time proving an inaccurate result or a waste of time due to an excessive reaction time. However, these problems can be solved using the device and the method according to the present disclosure.

After the elapse of the predetermined reaction time (adjusted reference time), the fluorescence signal emitted by scanning between the first position and the second position, that is, the membrane part E of the measurement window D is detected. The strip is exposed at the measurement window, and herein, it is possible to irradiate a light and collect the reflected light.

As a result, it is possible to shorten a total analysis time. That is, the analysis time (the time required for the lateral flow) is normally set to a uniform value which is somewhat more excessive than the actual time required for the assay to eliminate the inaccuracy resulting from the insufficient analysis time. However, when the start and the end time of the analysis can be accurately measured as in the device according to the present disclosure, the reaction/analysis time can be adjusted for each sample, rather than the reaction time uniformly applied to all the antigen-antibody reactions, thus eventually reducing the total analysis time.

In this regard, the present disclosure also relates to a method for adjusting the analysis time of a sample in the lateral flow assay by using a cartridge having a strip mounted therein and a measurement window through which a part of the strip is exposed.

The method according to the present disclosure comprises the following steps: a step of starting a lateral movement through a strip by loading the sample on the strip, in which the strip includes a sample pad on which the sample is loaded, a membrane through which the sample is developed, and an absorption pad; a step of measuring a first time which is a time that the sample laterally moving through the membrane reaches a first position of a measurement window; a step of measuring a second time which is a time that the sample reaches a second position of the measurement window and calculating a determined unit time required for the lateral flow per cm of the membrane by using a difference between the first time and the second time and the length of the measurement window; a step of obtaining a value by comparing the determined unit time with a given unit time provided by a membrane manufacturer; and calculating a minimum reaction time by multiplying the value by a total length of the membrane.

In the method according to the present disclosure, the first time and the second time are timed when the frontline of the liquid sample moving through the membrane by a lateral flow first reaches the membrane position corresponding to the first position and the second position of the measurement window, respectively, and these are measured by the device according to the present disclosure.

The fluorescence reader according to the present disclosure includes an optimum configuration for implementing the above-described method, and the method may be implemented by hardware, firmware, or software or a combination thereof for implementation. When it is implemented using a software, a storage medium includes any medium for storing or transmitting forms readable by a device such as a computer. For example, the computer-readable medium may include a read only memory (ROM); a random access memory (RAM); a magnetic disk storage medium; an optical storage medium; a flash memory device, and other electrical, optical or acoustic signal transmission medium, etc.

Figure 16:
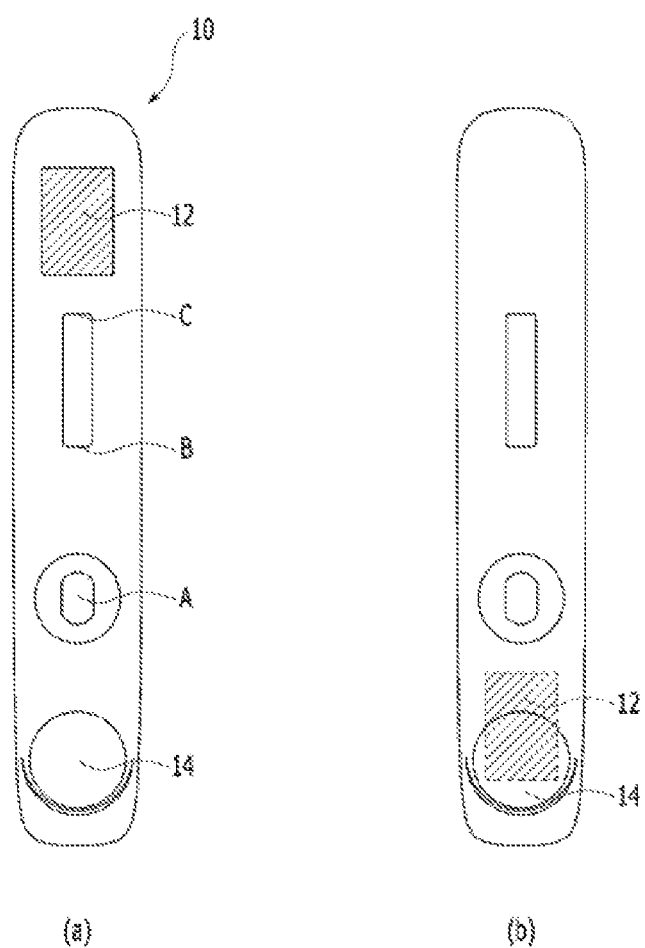
FIG. 16 is a diagram illustrating the cartridge 10 of one embodiment, which includes the sample inlet A, the first and second positions B, C of the measurement window, the membrane D, a handle 14, and a tag 12, used in the fluorescence reader according to one embodiment of the present disclosure; and (a) of FIG. 16 is a diagram illustrating that the tag is included outside of one end of the cartridge and (b) of FIG. 16 is a diagram illustrating that the tag is included inside of the other end of the cartridge.
Figure 17:
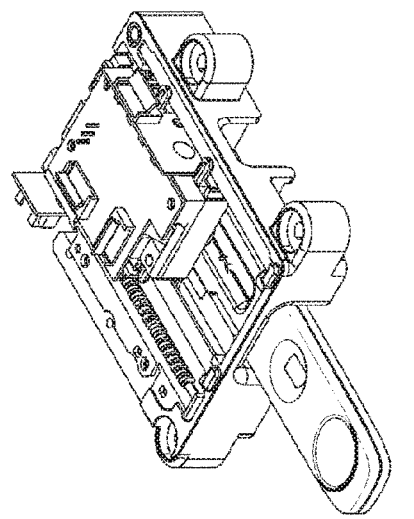
FIG. 17 is a diagram illustrating a perspective view and a lower side surface view of the present fluorescence reader (a) before and (b) after the cartridge (10) having the tag of (a) of FIG. 16 being inserted thereto. And it also illustrates a structure of a tag reader module 500 provided in the fluorescence reader depending on the positon of the tag.
Figure 17:
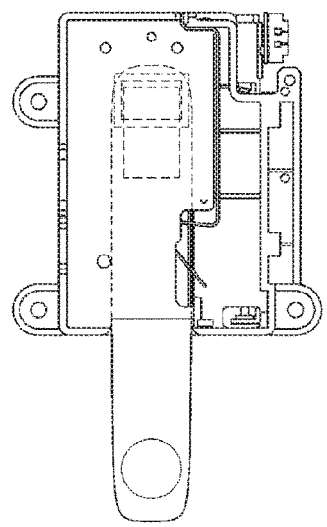
Figure 17:
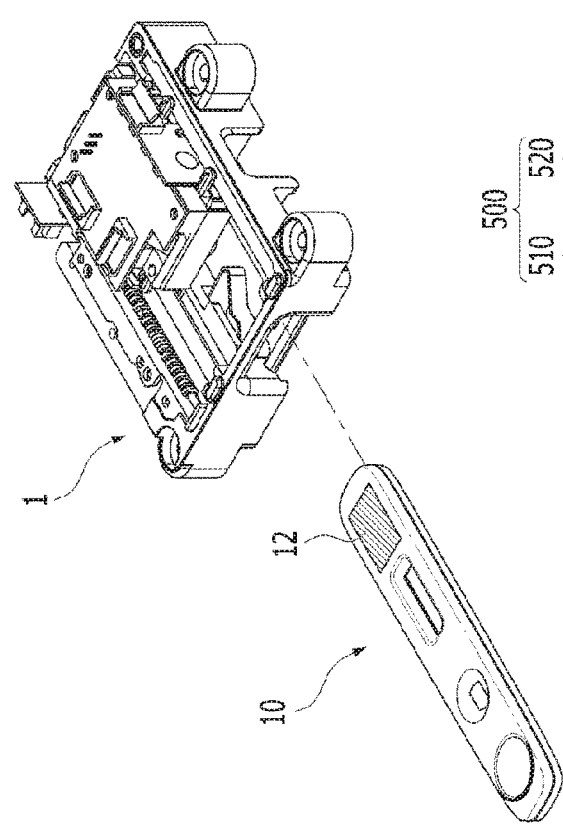
Figure 17:
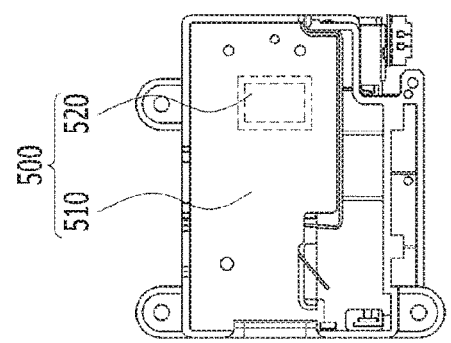
Figure 17:
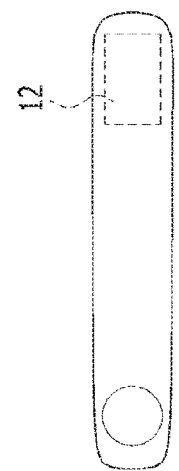
Figure 18:
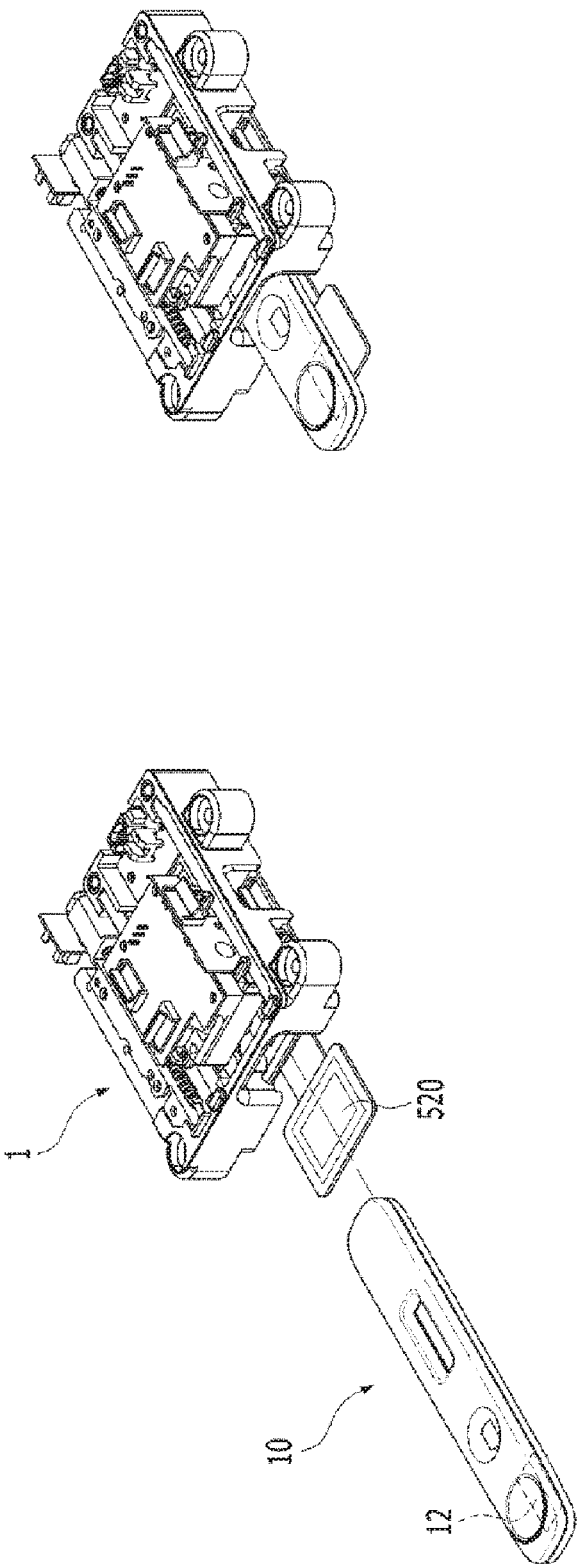
FIG. 18 is a diagram illustrating a perspective view and a lower side surface view of the present fluorescence reader (a) before and (b) after the cartridge (10) having the tag of (b) of FIG. 16 being inserted thereto. And it also illustrates a structure of a tag reader module 500 provided in the fluorescence reader depending on the positon of the tag.
Figure 18:
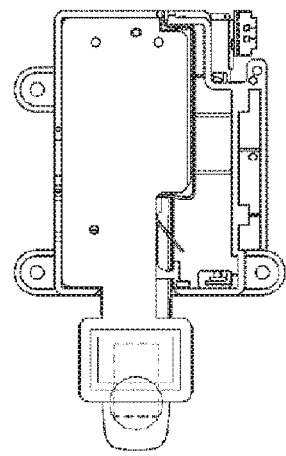

FIG. 16 is a diagram illustrating an example of the diagnostic cartridge 10 having a tag used in the fluorescence reader 1 according to an embodiment of the present disclosure, and FIGS. 17 and 18 are diagrams illustrating examples of fluorescence reader 1 and the diagnostic cartridge 10 according to an embodiment of the present disclosure.

The tag 12 for near-field communication may be provided in the diagnostic cartridge 10 used in the fluorescence reader 1 according to an embodiment of the present disclosure. Therefore, the fluorescence reader 1 according to an embodiment of the present disclosure may be configured to further include the tag reader module 500 for reading the tag 12.

The tag 12 is provided in the diagnostic cartridge 10. The tag 12 is a member capable of storing predetermined information. The tag 12 has, for example, a Near Field Communication (NFC) tag 12 to receive information and transmit the information using a Radio Frequency (RF) signal. The tag 12 is a kind of near-field communication method that has been internationally standardized.

The tag 12 may be attached to any position of the diagnostic cartridge 10. (a) of FIG. 16 is a diagram illustrating a shape in which the tag 12 is attached to one end portion of the diagnostic cartridge 10, and (b) of FIG. 16 is a diagram illustrating a shape in which the tag 12 is attached to a portion corresponding to the handle position inside the diagnostic cartridge 10.

As in (a) and (b) of FIG. 16, the tag 12 may be attached to the outside or the inside of the diagnostic cartridge 10, and may be attached to the end portion of the direction in which the diagnostic cartridge 10 is inserted into the fluorescence reader 1, or may also be attached to the opposite end portion, that is, to the portion of a handle 14 of the diagnostic cartridge 10. For example, when the tag 12 is attached to the inside of the diagnostic cartridge 10, the risk of damage to the tag 12 is reduced, thus reducing the risk of data loss due to a physical external force.

The tag reader module 500 is provided in the fluorescence reader 1. The tag reader module 500 is a device capable of reading the information held in the tag 12 provided in the diagnostic cartridge 10, and for example, may be configured to include a tag control part 510 for controlling the tag and a predetermined communication antenna 520, etc., which are implemented in a shape of a Printed Circuit Board (PCB), and the tag reader module 500, in particular, the communication antenna 520 may be disposed at the position corresponding to the position of the tag 12 when the diagnostic cartridge 10 has been inserted into the fluorescence reader 1 to read the information held in the tag 12. Therefore, the relative positions of the tag control part 510 and the tag antenna 520 in the tag reader module 500 may vary, and a structure of the tag module may be changed so as to receive it.

For example, as in (a) of FIG. 16, when the tag 12 is disposed adjacent to the end portion of the direction in which the diagnostic cartridge 10 is inserted into the fluorescence reader 1, as in FIG. 17, the tag antenna 520 is disposed to be placed further inwardly than the tag control part 510 in the insertion direction of the cartridge by comparing it with the tag control part 510. FIG. 17 shows (a) a diagram illustrating a state before the diagnostic cartridge 10 has been inserted into the fluorescence reader 1, and (b) a diagram illustrating a state after it has been inserted therein.

In another forms, as in (b) of FIG. 16, when the tag 12 is disposed at the opposite end portion in the direction in which the diagnostic cartridge 10 is inserted into the fluorescence reader 1, as in FIG. 18, the tag antenna 520 is disposed to be placed further outwardly in the insertion direction of the cartridge by comparing it with the tag control part 510. FIG. 18 shows (a) a diagram illustrating a state before the diagnostic cartridge 10 has been inserted into the fluorescence reader 1, and (b) a diagram illustrating a state after it has been inserted therein.

In general, the cartridge used in the device according to the present disclosure is used for the analysis based on lateral flow assay, and for this purpose, the membranes used for the lateral flow assay are manufactured with a nucleic acid material such as DNA, or a protein such as an antibody, or a labeled nucleic acids or proteins being attached thereto, which makes the manufacturing process complicated and makes it difficult to produce membranes with completely identical characteristics among different batches because even when the same process is used to make them, raw or base materials and other materials used for making the cartridges can be slightly different depending on various values such as the date of manufactured, etc.

Therefore, there arise needs for a method for compensating the difference to ensure reproducible results. Conventionally, in order to prevent such an error from occurring, a method has been used for setting various lot information including a name of a biomarker, an expiration date, a measurement unit, a parameter boundaries, etc., which are used in diagnosis, applying a processing formula corresponding thereto to store it in a predetermined storage, and reading it in the fluorescence reader. In such a conventional technology, it is normally stored in the form of a bar code or an external code chip, and a user scans the bar code, or inserts the corresponding memory into the fluorescence reader to compensate for a difference between lots to process the information.

However, in order to prevent errors by a user inserting a wrong storage memory therein, or using the same storage memory again even when the lot has been changed, or to reduce the burden that a user has to change the storage memory every time a box is changed because the lot information is not provided in the diagnostic cartridge, but is provided on the packaging box, the tag 12 can be advantageously used.

When utilizing the tag 12 and the tag reader module 500 according to the present disclosure, it is possible to resolve the inconvenience of utilizing the lot information, and at the same time, to also apply the information on the flow rate in combination with the lot information. That is, it is also possible to store the information on the sample flow rate according to a type of detection or for each lot therein, thus become flexible in applying the time according to the flow rate. For example, even if a difference between the flow rates of a detection method A and a detection method B is identical to 10 seconds, there may be a difference in calibration value applied in calculating the results between the two methods such that different calibration value 5% and 3% may be applied for method A and method B, respectively, depending on the lot information stored in tag 12, which provides an another advantage.

As described above, although the preferred embodiments of the present disclosure have been illustrated and described, various modifications may be made by those skilled in the art to which the present disclosure pertains without departing from the subject matter of the present disclosure, and in addition, the modifications should not be understood individually from the technical spirit or views of the present disclosure.

DETAILED DESCRIPTION OF MAIN ELEMENTS

1: fluorescence reader
10: cartridge
12: tag
14: handle
100: base frame
110: open part
120: insertion space
130: plate spring
200: optical module
210: module casing
212: upper casing 214: lower casing
216: guide part
217: upper guide
218: lower guide
220: light source
222: light source board
230: light sensor part
240: light guide part
242: first mirror
244: second mirror
246: downward lens
250: light processing part
252: emission filter
254: lens
256: pin hole
258: converter
260: interrupt protrusion part
270: laser heat-dissipating part
300: driving module
310: motor
312: motor board
320: driving shaft
322: spiral guide groove
330: carrier
331: first side
333: fixing groove
334: second side
335: guide protrusion part
336: curved surface of a "C" shape
338: upper protrusion part
339: lower protrusion part
340: elastic part
341: bent part
350: guide shaft
352: first guide shaft
354: second guide shaft
400: sensor module
410: main board
420: interrupt sensor
422: insertion groove
430: sensing switch
432: Illustration of a structure of the tag reader module 500 provided in the fluorescence reader according to the positions of a triangular button and a tag
440: connector
500: tag reader module
510: tag control part
520: tag antenna

The invention claimed is:

1. A fluorescence reader, comprising:
a base frame having an open part formed at the front thereof so that a diagnostic cartridge is inserted therein and having an inner space therein;
an optical module disposed in the inner space of the base frame, and disposed to be positioned above the diagnostic cartridge inserted through the open part to irradiate a light to the diagnostic cartridge;
a driving module for moving the optical module; and
a sensor module for sensing the insertion of the diagnostic cartridge and the position of the optical module,
wherein the driving module comprises:
a motor for providing a rotational force;
a driving shaft rotatably connected to the motor and disposed outside of the optical module to be extended along a front-rear direction of the driving shaft; and
a carrier disposed between the optical module and the driving shaft to be coupled to the optical module and connected to the driving shaft,
wherein the driving shaft has a spiral guide groove spirally extending along an outer surface thereof, and
wherein the carrier has a guide protrusion part having one side coupled to one side of the optical module and having the other side inserted into the spiral guide groove,
such that when the motor rotates to thereby rotate the driving shaft, the guide protrusion part is pushed by the spiral guide groove in the front-rear direction to displace the carrier in the front-rear direction, and accordingly, the optical module connected to the carrier is displaced in the front-rear direction.

2. The fluorescence reader of claim 1,
wherein the optical module comprises
a module casing having a predetermined inner space therein;
a light source disposed in the module casing and for generating excitation light;
a light sensor part disposed in the module casing and for receiving emitted light generated from the diagnostic cartridge;
a light guide part disposed in the module casing and for guiding the excitation light and the emitted light; and
a light processing part for processing the incident emitted light,
wherein the light guide part is configured to include one or more lens parts and mirrors to guide so that the excitation light generated from the light source is irradiated on the diagnostic cartridge, and to guide so that the emitted light generated from the diagnostic cartridge is incident to the light sensor part.

3. The fluorescence reader of claim 2,
wherein the module casing is configured to have a rectangular box shape having an inner space therein,
wherein the light source is disposed on a lateral one surface of the inner surface of the module casing,
wherein the light sensor part is disposed on a rear one surface of the inner surface of the module casing,
wherein the light guide part is configured to include a first mirror, a second mirror, and a downward lens; and the first mirror refracts the excitation light irradiated laterally from the light source in the front direction thereof, the second mirror downwardly refracts the excitation light refracted in the front direction thereof, and the downward lens is configured so that the excitation light refracted downwardly passes therethrough to be irradiated on the diagnostic cartridge disposed under the lens, and
wherein the light processing part is configured to include an emission filter, a lens, and a pin hole; and the emission filter, the lens, and the pin hole are sequentially disposed between the first mirror and the light sensor part in the front-rear direction thereof to be disposed on a line that is lined with the first mirror, the second mirror, and the light sensor part.

4. The fluorescence reader of claim 3,
wherein the emitted light generated from the diagnostic cartridge is incident to the second mirror upwardly by passing through the downward lens, and is refracted by the second mirror backwardly to be incident to the first mirror,
wherein the first mirror is made of a dichroic mirror so that the emitted light pass through the first mirror in the rear direction thereof, and wherein the emitted light passes through the emission filter, the lens, and the pin hole to be incident to the light sensor part.

5. The fluorescence reader of claim 2,
wherein the optical module is made of a heat-dissipating material and further comprises a laser heat-dissipating part closely contacting at least one surface of the light source.

6. The fluorescence reader of claim 2,
wherein the module casing has a guide part on at least one side thereof, the guide part being protruding laterally, and
wherein the guide part comprises an upper guide, a lower guide disposed under the upper guide being parallel with the upper guide, and a side guide disposed between the upper guide and the lower guide vertically formed on the outside.

7. The fluorescence reader of claim 2,
wherein the sensor module comprises
a main board fixed to the base frame; and
an interrupt sensor disposed on the main board,
wherein the optical module further comprises an interrupt protrusion part disposed to be protruded on the rear outside of the module casing,
wherein the open part and the interrupt sensor, each is disposed in the opposite direction along the front-rear direction of the casing, and
wherein the optical module has an initial position in which the interrupt protrusion part is inserted into the interrupt sensor, and changes the position between the position of the open part and the position of the interrupt sensor.

8. The fluorescence reader of claim 7,
wherein the sensor module further comprises a sensing switch disposed under the main board, and
wherein the sensing switch generates an insertion signal that the diagnostic cartridge is inserted by being configured to have the diagnostic cartridge press the sensing switch when an end portion of the diagnostic cartridge reaches a particular position after the diagnostic cartridge is inserted into the base frame through the open part.

9. The fluorescence reader of claim 1,
wherein the guide protrusion part has a plurality of protrusions protruded laterally and extended obliquely, and has a configuration of a curved surface of a "C" shape in which the side surface thereof is recessed to the inside thereof and the driving shaft is disposed in the curved surface of the "C" shape.

10. The fluorescence reader of claim 1,
wherein the carrier has an elastic part configured to have a plurality of bent parts between a first side coupled to the optical module and a second side having the guide protrusion part,
such that the second side contacts closely the driving shaft and the guide protrusion part is stably inserted into the spiral guide groove.

11. The fluorescence reader of claim 1,
wherein the driving module further comprises a guide shaft extended in the front-rear direction thereof and disposed between the driving shaft and the optical module,
wherein the carrier has a guide hole penetrated in the front-rear direction thereof, and
wherein the guide shaft is configured to penetrate the guide hole so that the front-rear directional displacement of the carrier and the driving module are guided by the guide shaft.

12. The fluorescence reader of claim 1,
wherein the base frame further comprises a plate spring at least a part of which being protruded into a insertion space, and
wherein the plate spring put a pressure on at least a part of the diagnostic cartridge to fix the position of the diagnostic cartridge when the diagnostic cartridge is inserted into the insertion space.

13. The fluorescence reader of claim 1,
wherein the diagnostic cartridge comprises a measurement window extended in the direction of the lateral flow of a sample exposing the lateral flow of the sample, and
wherein the optical module moves to the end point of the measurement window after sensing the start time of the lateral flow of the sample at the start point of the measurement window, and
detects the end time of the lateral flow of the sample at the end point of the measurement window to calculate a rate of the lateral flow.

14. The fluorescence reader of claim 1,
wherein the diagnostic cartridge is provided with a tag for storing a predetermined information, and wherein the fluorescence reader further comprises a tag reader module capable of reading the tag provided in the diagnostic cartridge.

15. A method for adjusting an analysis time of a sample in a lateral flow assay,
wherein the lateral flow assay is performed using a cartridge having a strip mounted therein and a measurement window for exposing at least part of the strip where the sample develops,
the method comprising:
starting a lateral movement of the sample through the strip by loading the sample on the strip, the strip comprising a sample pad on which the sample is loaded, a membrane through which the sample is developed, and an absorption pad,
measuring a first time that is a time at which the sample starts the lateral flow to reach a first position of the measurement window;
measuring a second time that is a time at which the sample reaches a second position of the measurement window, and calculating a determined unit time required for the lateral flow to happen per membrane cm by using a difference between the first time and the second time and the length of the measurement window;
obtaining a value by comparing the determined unit time and a given unit time provided by a membrane manufacturer; and
calculating a minimum reaction time by multiplying the value by a total length of the membrane.

* * * * *